United States Patent
Sanet et al.

(10) Patent No.: US 10,234,441 B2
(45) Date of Patent: Mar. 19, 2019

(54) WATER IN FUEL (WIF) SENSOR HAVING ELECTROSTATIC DISCHARGE CAPABILITY

(71) Applicant: SOGEFI Engine Systems USA, Inc., Rochester Hills, MI (US)

(72) Inventors: Fabien Sanet, Rochester Hills, MI (US); Yann Berland, Ablis (FR)

(73) Assignee: Sogefi Engine Systems USA, Inc., Rochester Hills, MI (US)

(*) Notice: Subject to any disclaimer, the term of this patent is extended or adjusted under 35 U.S.C. 154(b) by 36 days.

(21) Appl. No.: 15/267,805

(22) Filed: Sep. 16, 2016

(65) Prior Publication Data

US 2018/0080916 A1 Mar. 22, 2018

(51) Int. Cl.
*G01N 33/28* (2006.01)
*G01N 27/07* (2006.01)
*B01D 36/00* (2006.01)

(52) U.S. Cl.
CPC ....... *G01N 33/2847* (2013.01); *B01D 36/005* (2013.01); *G01N 27/07* (2013.01)

(58) Field of Classification Search
CPC ............................ G01N 33/2847; G01N 27/07
See application file for complete search history.

(56) References Cited

U.S. PATENT DOCUMENTS

| | | |
|---|---|---|
| 3,988,668 A | 10/1976 | Bowers |
| 6,168,713 B1 | 1/2001 | Sekine et al. |
| 6,245,231 B1 | 6/2001 | Maki et al. |
| 6,452,394 B1 * | 9/2002 | Lappalainen ...... G01R 33/3628 324/307 |
| 6,740,236 B2 | 5/2004 | Rickle et al. |
| 7,855,559 B2 * | 12/2010 | DeFranco .......... G01R 33/3657 324/322 |
| 8,182,682 B1 | 5/2012 | Rajadhyaksha et al. |
| 8,431,023 B2 | 4/2013 | Berland et al. |
| 8,598,878 B2 * | 12/2013 | Taracila ............. G01R 33/3628 324/318 |
| 9,072,992 B2 | 7/2015 | Mendel et al. |

(Continued)

FOREIGN PATENT DOCUMENTS

| | | |
|---|---|---|
| WO | 2012/076872 | 6/2012 |
| WO | 2015/057809 | 4/2015 |

OTHER PUBLICATIONS

EP, Extended European Search Report and Opinion; Application No. 17191302.3, 9 pages (dated Dec. 4, 2017).

*Primary Examiner* — Tung X Nguyen
*Assistant Examiner* — Dominic Hawkins
(74) *Attorney, Agent, or Firm* — Warner Norcross & Judd LLP

(57) ABSTRACT

A water in fuel (WIF) sensor is disclosed, and comprises a main body defining a surface, a pair of electrical contacts, and a third electrical contact assembly. The pair of electrical contacts each have a first end portion that is located along the surface of the main body. A predetermined resistance flows between the electrical contacts when the first end portions of the electrical contacts are submerged in water. The third electrical contact assembly has a first end portion and a second end portion. The first end portion of the third electrical contact assembly is located along the surface of the main body and the second end portion of the third electrical contact assembly is connectable to a ground.

20 Claims, 5 Drawing Sheets

(56) References Cited

U.S. PATENT DOCUMENTS

| | | | |
|---|---|---|---|
| 9,182,468 B2* | 11/2015 | Kaneko | G01R 33/5659 |
| 9,403,110 B2 | 8/2016 | Gwin et al. | |
| 2006/0219004 A1 | 10/2006 | Forgue | |
| 2009/0009169 A1* | 1/2009 | Schulz | G01R 33/34046 |
| | | | 324/318 |
| 2010/0089805 A1* | 4/2010 | South | B01D 35/30 |
| | | | 210/86 |
| 2011/0259802 A1* | 10/2011 | Wieczorek | B01D 36/005 |
| | | | 210/96.1 |
| 2012/0103910 A1* | 5/2012 | Ferrari | B01D 17/0202 |
| | | | 210/669 |
| 2013/0031963 A1* | 2/2013 | Ritchie, Jr. | G01N 33/2847 |
| | | | 73/61.43 |
| 2013/0284675 A1* | 10/2013 | Core | B01D 17/0202 |
| | | | 210/691 |
| 2013/0285678 A1* | 10/2013 | Gwin | B01D 36/005 |
| | | | 324/656 |
| 2016/0067639 A1* | 3/2016 | Shimpi | F02D 41/22 |
| | | | 210/85 |
| 2016/0215740 A1 | 7/2016 | Chretien et al. | |
| 2016/0296864 A1* | 10/2016 | Shimpi | B01D 35/143 |

* cited by examiner

WATER IN FUEL (WIF) SENSOR HAVING ELECTROSTATIC DISCHARGE CAPABILITY

FIELD OF THE INVENTION

The present invention generally relates to a water in fuel (WIF) sensor having electrostatic discharge capabilities. In particular, the present invention is directed to a WIF sensor having an additional electrical contact that dissipates electrostatic charges accumulated by a filter.

DESCRIPTION OF THE RELATED ART

In the area of automotive components, fuel filters may be placed within a housing or canister and are used to remove contaminates from fuel such as, for example, paint chips and rust particles. Those of ordinary skill in the art will readily appreciate that fuel injectors have relatively small openings that are precision machined. The functioning of the injectors depends in part on the fuel that is delivered to the injector being free of contaminates. Thus, fuel filters are provided to screen out particles that may block the injectors.

In some types of vehicles, a resistance heating system may be provided along a top portion of the fuel canister, and is used to heat the fuel. Specifically, fuel may flow into the canister and through the resistance heating system. The warmed fuel then flows through the filter and then exits the canister. It is to be appreciated that as fuel passes through the filter, static electricity may be generated. In one approach to dissipate static electricity from the fuel filter, a grounding connector may be placed between an upper cap of the filter and the resistance heating system. The resistance heating system may be connected to an engine control unit (ECU). In another approach, the grounding connector may be placed between the upper cap of the filter and another electrical component included within the canister, such as an electrical pump or a sensor that is connected to the ECU. However, linking the filter element to the ECU for grounding may not always be feasible if the canister does not include electrical features such as a resistance heater, an electrical pump, or various sensors.

If water enters the canister, the water may settle below the fuel in the canister since water is denser than fuel. A water in fuel (WIF) sensor may be used to determine if the water settled in the canister has reached a certain depth within the canister. The WIF sensor may be secured to a bottom portion of the canister, where a portion of the WIF sensor extends into the interior of the canister. The WIF sensor may include two electrically conductive pins, where the ends of the pins extend into the bottom portion of the interior of the canister. When the depth of the water in the canister is of a sufficient level such that water contacts the ends of both pins, then electricity flows from one pin, through the water, and to the other pin. Although inclusion of a WIF sensor is not mandatory, it is to be appreciated that increasing number of fuel filtering systems are requiring a WIF sensor to be placed within the canister to detect a threshold level of water inside the canister.

BRIEF SUMMARY OF THE INVENTION

In one embodiment, a water in fuel (WIF) sensor is disclosed. The WIF sensor comprises a main body defining a surface, a pair of electrical contacts, and a third electrical contact assembly. The pair of electrical contacts each have a first end portion that is located along the surface of the main body. A predetermined resistance flows between the electrical contacts when the first end portions of the electrical contacts are submerged in water. The third electrical contact assembly has a first end portion and a second end portion. The first end portion of the third electrical contact assembly is located along the surface of the main body and the second end portion of the third electrical contact assembly is connectable to a ground.

In another embodiment, a fuel filtering system is disclosed, and comprises a filter element, a housing, and a WIF sensor. The housing contains the filter. The housing defines a wall, where the housing defines an aperture. The aperture of the housing is shaped to receive the WIF sensor. The WIF sensor comprises a main body defining a surface where the surface is located within the housing, a pair of electrical contacts, and a third electrical contact assembly. The electrical contacts each have a first end portion that is located along the surface of the main body. A predetermined resistance flows between the electrical contacts when the first end portions of the electrical contacts are submerged in water. The third electrical contact assembly has a first end portion and a second end portion. The first end portion of the third electrical contact assembly is located along the surface of the main body and is electrically connected to the filter element. The second end portion of the third electrical contact assembly is connectable to a ground.

BRIEF DESCRIPTION OF THE DRAWINGS

For the purpose of illustrating the invention, the drawings show a form of the invention that is presently preferred. However, it should be understood that the present invention is not limited to the precise arrangements and instrumentalities shown in the drawings, wherein.

DETAILED DESCRIPTION

Figure 1:
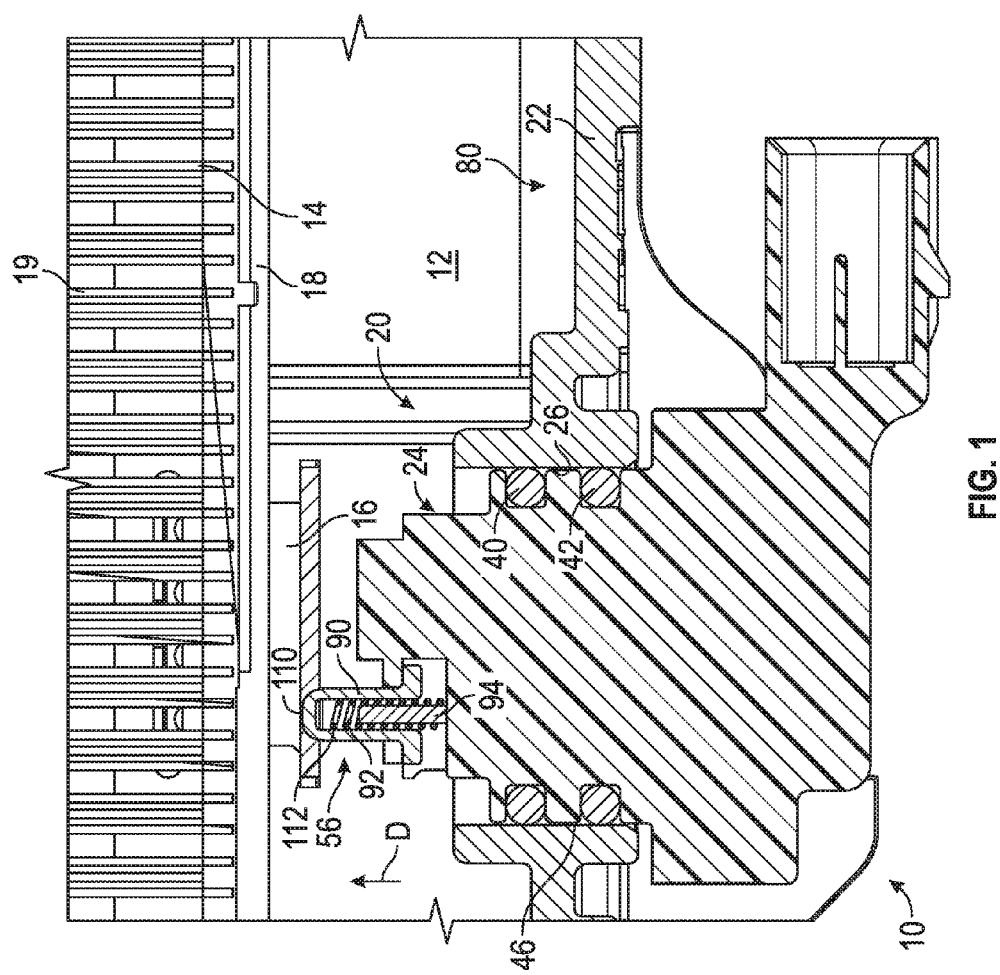
FIG. 1 is a cross-sectioned view of a housing containing a filter element, where a water in fuel (WIF) sensor may be located along a bottom wall of the housing.

Referring now to the drawings in which like reference numerals indicate like parts, FIG. 1 illustrates a portion of an exemplary canister or housing 10. The housing 10 defines an interior cavity 12. As seen in FIG. 1, various components such as a filter element 14 and a part 16 may be placed within the interior cavity 12 of the housing 10. The part 16 may be any component constructed of a conductive material. In one embodiment, the filter element 14 may have a top end cap (not shown) and a bottom end cap 18. In the embodiment as illustrated, at least the bottom end cap 18 is constructed of an electrically dissipative or conductive material such as, for example, metal or a carbon filled plastic material. A fiber media 19 may be disposed between the top and bottom end cap 18 of the filter element 14. In one embodiment, fuel may flow from through the filter element 14 and through the fiber media 19 for filtering out contaminates from fuel. The part 16 may be any component constructed of an electrically conductive material, where the part 16 is electrically connected to the bottom end cap 18 of the filter element 14. Alternatively, the part 16 may be electrically connected to the filter element 14. A water in fuel (WIF) sensor 20 may be located along a bottom wall 22 of the housing 10. Specifically, the bottom wall 22 of the housing 10 may define an aperture 26 that is shaped to receive the WIF sensor 20. A portion 24 of the WIF sensor 20 may extend into the interior cavity 12 of the housing 10.

Figure 2:
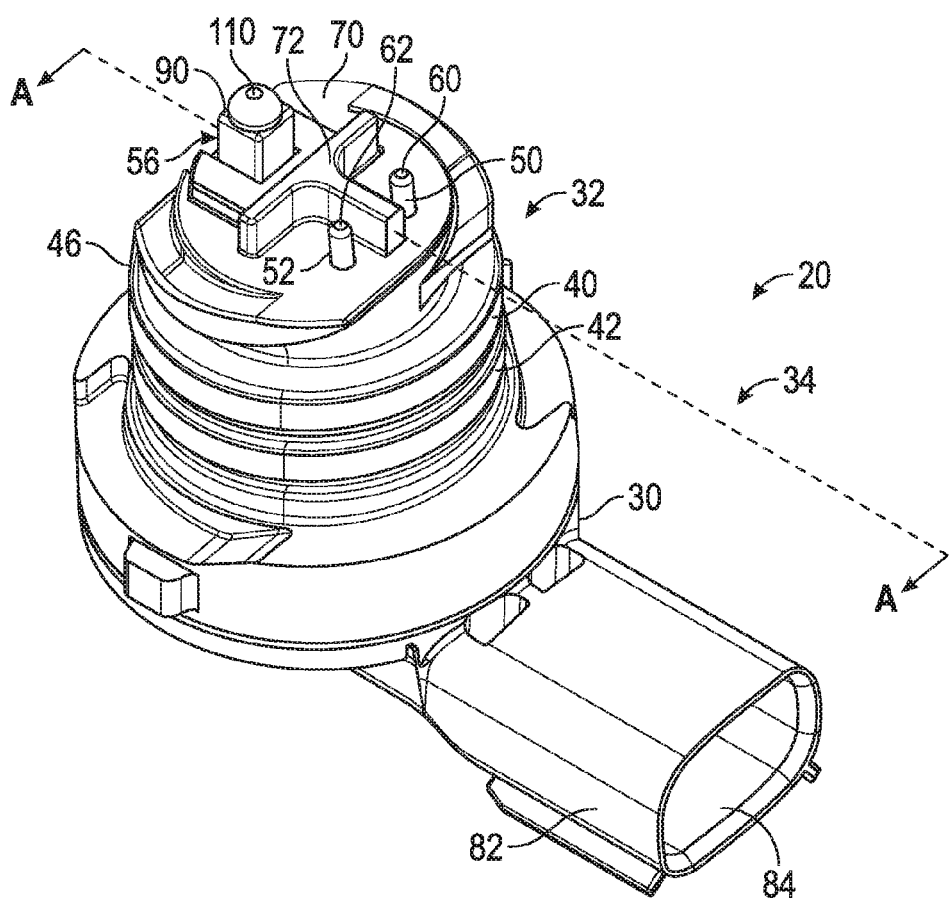
FIG. 2 is an elevated perspective view of the WIF sensor shown in FIG. 1, where the WIF sensor includes three electrical contacts.

FIG. 2 is an elevated perspective view of the WIF sensor 20 shown in FIG. 1. The WIF sensor 20 may include a body 30 constructed of a non-conductive material such as, for example, plastic. The body 30 of the WIF sensor 20 may define a first portion 32 and a second portion 34. The first portion 32 of the WIF sensor 20 may have a generally cylindrical profile, however it is to be appreciated that the illustration shown in FIG. 2 is merely exemplary in nature and the WIF sensor 20 may include other shapes as well. In one non-limiting embodiment, the WIF sensor 20 may include one or more O-rings 40, 42 that surround an outer circumference 46 of the first portion 32 of the WIF sensor 20. As seen in FIGS. 1 and 2, the O-rings 40, 42 may be used to provide a fluid-tight seal between the aperture 26 located along the bottom wall 22 of the housing 10 and the outer circumference 46 of the WIF sensor 20. However, it is to be appreciated that in some embodiments, the O-rings 40, 42 may be omitted as well.

Figure 3:
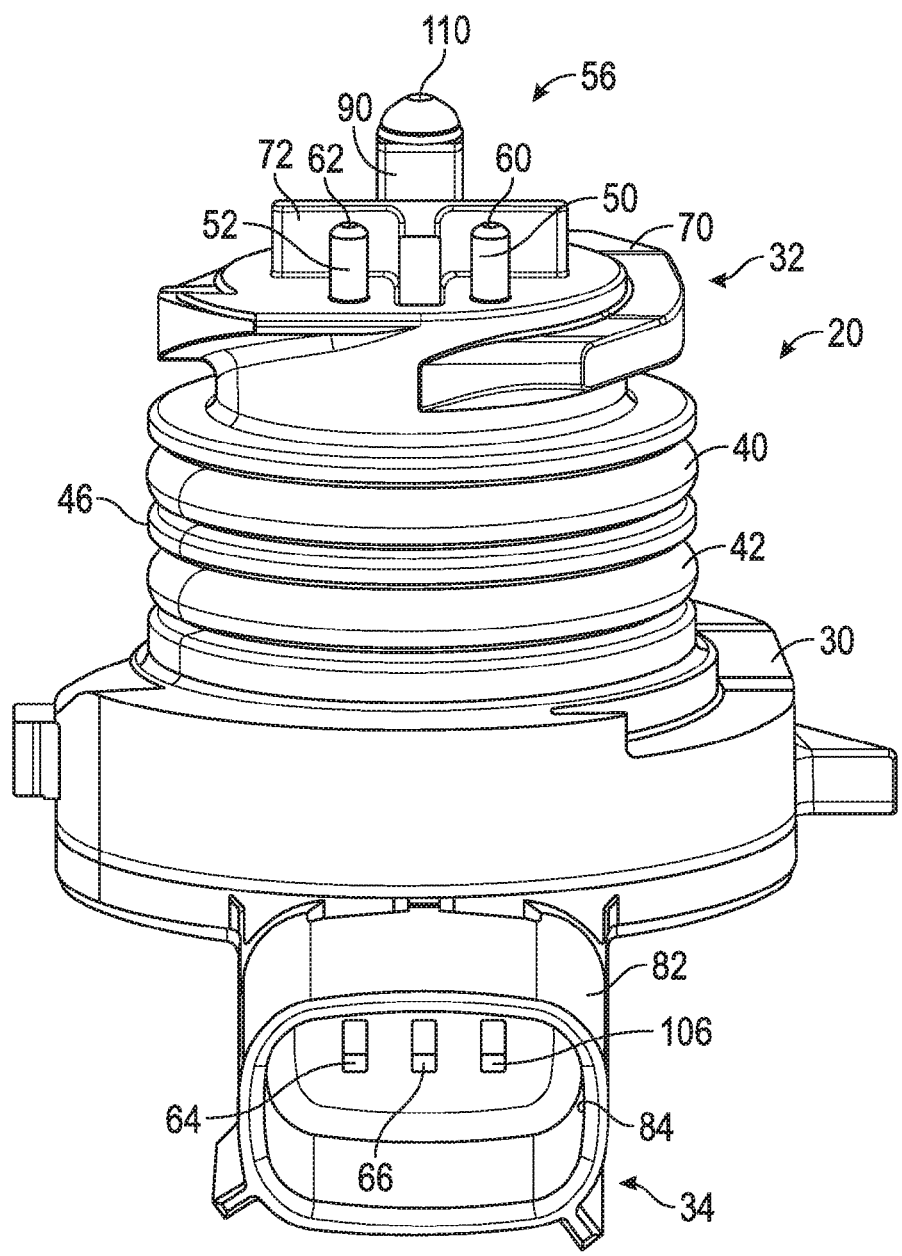
FIG. 3 is a front view of the WIF sensor shown in FIG. 1.
Figure 4:
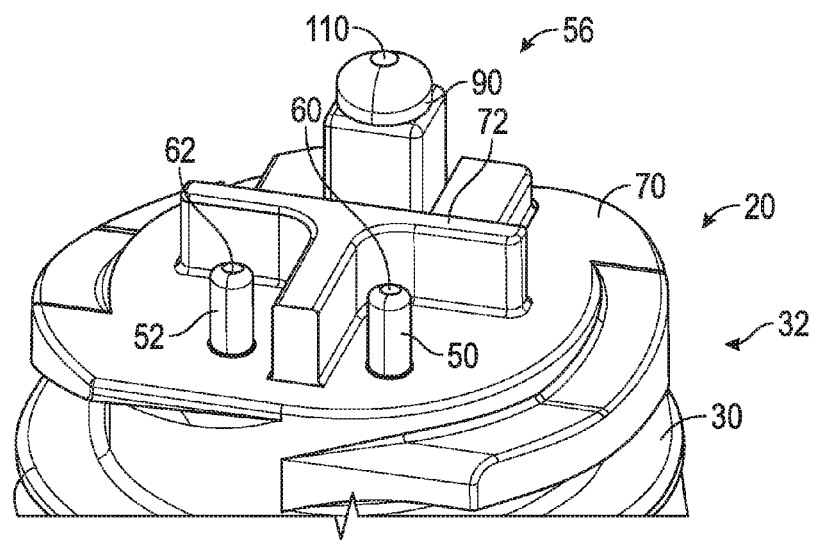
FIG. 4 is an enlarged view of a top portion of the WIF sensor shown in FIG. 1.

The WIF sensor 20 includes three electrical contacts. Specifically, the WIF sensor 20 may include a pair of electrical contacts 50, 52 as well as a third electrical contact assembly 56. As explained in greater detail below, the electrical contacts 50, 52 may be used to detect the presence of water within the housing 10, and the third electrical contact assembly 56 may be used to dissipate static electricity from the filter element 14. The electrical contacts 50, 52 may be elongated metal pins that extend through the body 30 of the WIF sensor 20. Referring to FIGS. 1-3, the electrical contacts 50, 52 include first end portions 60, 62 as well as second end portions 64, 66. The first end portions 60, 62 of the electrical contacts 50, 52 may be located along a top surface 70 of the WIF sensor 20. Turning now to FIG. 4, a wall or partition 72 may project outward from the top surface 70 of the WIF sensor 20. In the exemplary embodiment as shown in FIG. 4, the wall 72 may be generally "T" shaped and provides a non-conductive barrier between the two electrical contacts 50, 52.

Referring to FIGS. 1, 2 and 4, the first end portions 60, 62 of the electrical contacts 50, 52 may extend into the interior cavity 12 of the housing 10 when the WIF sensor 20 is installed to the housing 10. Specifically, the first end portions 60, 62 of the electrical contacts 50, 52 may be positioned along a bottom portion 80 of the housing 10 once the WIF sensor 20 is installed. During conditions where water is not present along the bottom portion 80 of the housing 10, the electrical contacts 50, 52 are not electrically connected to one another. Thus, an open circuit condition exists between the two electrical contacts 50, 52. If water enters the housing 10, the water may collect along the bottom portion 80 of the housing 10. The WIF sensor 20 may determine if the water settled along the bottom portion 80 of the housing 10 has reached a predetermined depth. Specifically, when the depth of the water in the housing 10 is of a sufficient level such that water contacts the first end portions 60, 62 of both electrical contacts 50, 52, then electricity flows from one contact 50, through the water, and to the other contact 52 because of the relatively high conductivity of the water. In other words, the first end portions 60, 62 of both electrical contacts 50, 52 are electrically connected by the water, which also provides a relatively low level of resistance to current flow.

Figure 7:
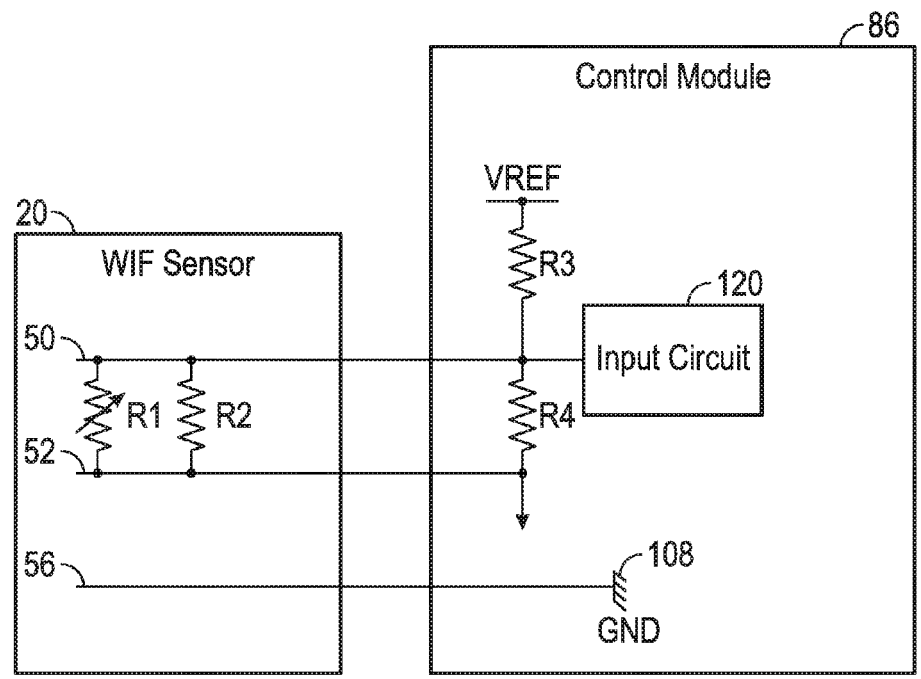
FIG. 7 is an electrical schematic diagram of the WIF sensor electrically connected to a control module.

Turning back to FIGS. 2 and 3, the housing 30 of the WIF sensor 20 may define an electrical socket or connector 82. The connector 82 may be located at the second portion 34 of the WIF sensor 20, where the connector 82 defines a cavity 84. The cavity 84 may be shaped to receive a corresponding plug (not illustrated) of a control module 86 (FIG. 7). The control module 86 may refer to, or be part of, an application specific integrated circuit (ASIC), an electronic circuit, a combinational logic circuit, a field programmable gate array (FPGA), a processor (shared, dedicated, or group) comprising hardware or software that executes code, or a combination of some or all of the above, such as in a system-on-chip. In one embodiment, the control module 86 may be an engine control unit (ECU) or a powertrain control module (PCM), however it is to be appreciated that these modules are merely exemplary in nature.

The second end portions 64, 66 of the electrical contacts 50, 52 may be located within the cavity 84 of the connector 82, and may be electrically connected to the control module 86. The control module 86 may be programmed to monitor the total resistance across the first end portions 60, 62 of the electrical contacts 50, 52, and to compare the resistance with one or more resistance values stored within memory. The memory may have resistance values that correspond to a situation where the first end portions 60, 62 of the electrical contacts 50, 52 are submerged in water. A predetermined resistance flows between the electrical contacts 50, 52 when the first end portions 60, 62 are submerged in water. Thus, when the first end portions 60, 62 of the electrical contacts are electrically connected to one another by water and indicate the predetermined resistance that corresponds to the electrical connection, the control module 86 may communicate the presence of water in the housing 10 (FIG. 1) to an output device (not illustrated). For example, in one embodiment the output device may be a warning light located on a dashboard display of a vehicle.

Figure 5:
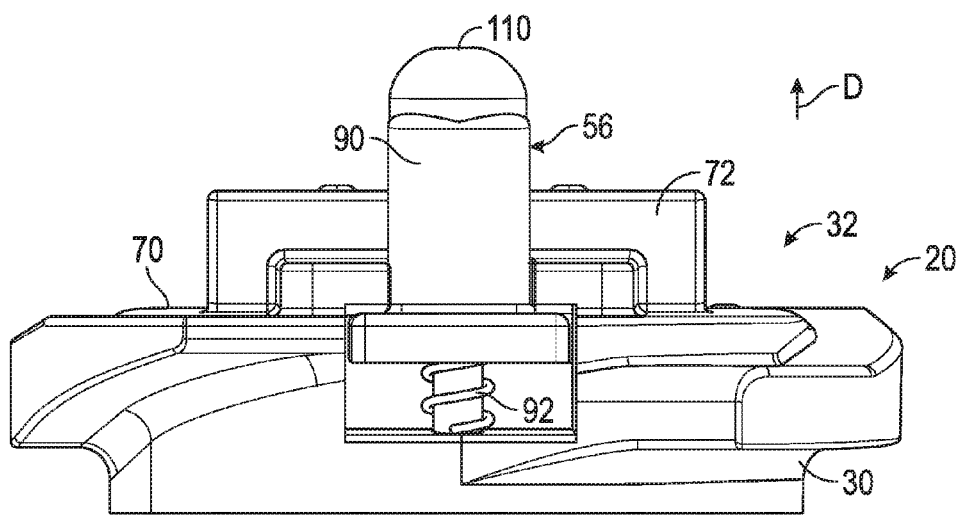
FIG. 5 is an enlarged front view of the top portion of the WIF sensor.
Figure 6:
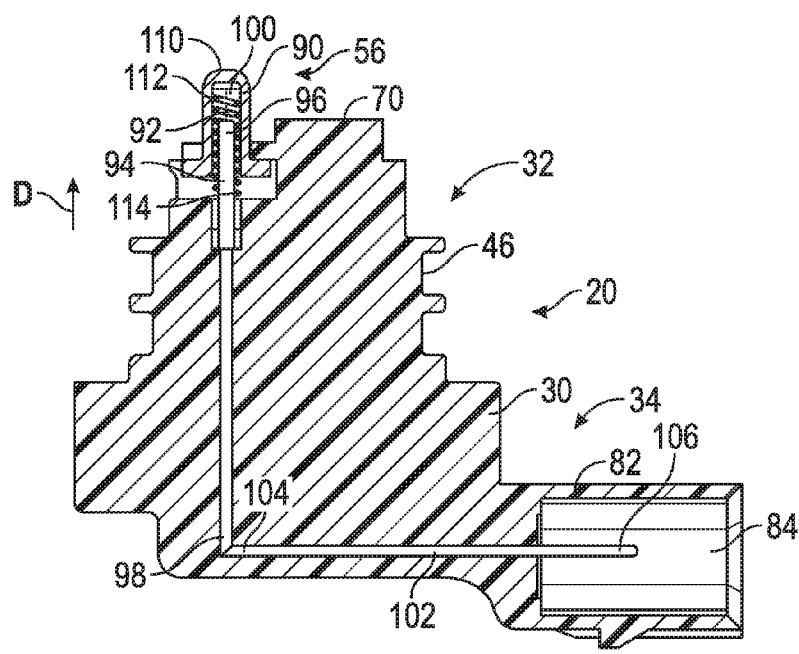
FIG. 6 is a cross-sectioned view of the WIF sensor taken along section A-A in FIG. 2.

FIG. 5 is an enlarged view of an upper portion of the WIF sensor 20 including the third electrical contact assembly 56. In the exemplary embodiment as shown, the third electrical contact assembly 56 is biased in an upwards direction D, however it is to be appreciated that the third electrical contact assembly 56 may not be biased as well. FIG. 6 is a cross-sectioned view of the WIF sensor 20 taken along section A-A in FIG. 2. In the exemplary embodiment illustrated in FIGS. 5-6, the third electrical contact assembly 56 may include a hollow pin 90, a biasing element 92, a pin 94, and a pin 102. The pin 94 may be an elongated pin that extends partially through the body 30 of the WIF sensor 20. As seen in the cross-sectioned view of the WIF sensor 20 in FIG. 6, the pin 94 includes a first end 96 and a second end 98, where the first end 96 is located within a cavity 100 defined by the hollow pin 90. The pin 94 extends through the body 30 of the WIF sensor 20, and the second end 98 of the pin 94 may be in electrical contact with the elongated pin 102.

In the embodiment as illustrated, the pin 102 may include a first end portion 104 and a second end portion 106. The first end portion 104 of the pin 102 may abut against or otherwise be in electrical contact with the second end 98 of the pin 94. As seen in the non-limiting embodiment of FIG. 6, the pin 102 may extend through the body 30 of the WIF sensor 20 in a direction that is substantially perpendicular to the pin 94. The pin 102 terminates at the second end 106. The second end 106 of the pin 102 may be located within the cavity 84 of the connector 82.

Referring to FIGS. 3, 6 and 7, the second end 106 of the pin 102 may be electrically connected to the control module 86. The pin 102 may be connected to earth or ground 108 of the control module 86. The hollow pin 90, the biasing element 92, the pin 94, and the pin 102 are each constructed of an electrically conductive material such as, but not limited to, metal. As seen in FIG. 1, the hollow pin 90 defines a top surface 110 that abuts or otherwise electrically contacts the part 16. The part 16 is electrically connected to the bottom end cap 18 and to the filter media 19 of the filter element 14. Thus, static electricity that is generated in the filter element 14 may travel through the bottom end cap 18 and/or through the filter media 19, to the part 16, through the hollow pin 90 to the biasing element 92, from the biasing element 92 to the pin 94, and from the pin 94 to the pin 102. The static electricity may then travel from the pin 102 to the ground 108 of the control module 86. Thus, it is to be appreciated that the third electrical contact assembly 56 may be used to dissipate static electricity from the filter element 14.

It is to be appreciated that while FIG. 1 illustrates the part 16, the top surface 110 of the hollow pin 90 may directly contact the bottom end cap 18 of the filter element 14 instead, as long as the bottom end cap 18 is constructed of an electrically dissipative material. In another embodiment, the top surface 110 of the hollow pin 90 may directly contact the filter media 19. In still another embodiment, the hollow pin 90 may directly contact the top end cap (not illustrated in the figures), as long as the top end cap is constructed of an electrically conductive material. Furthermore, it should also be appreciated that the embodiment as shown in FIG. 1 is merely exemplary in nature, and the top surface 110 of the hollow pin 90 may directly contact any number of components that are electrically connected to the filter element 14 as well.

Referring to FIGS. 1 and 6, the biasing element 92 may be any type of element for exerting a biasing force upon the hollow pin 90 in an upwards direction D, and towards the filter element 14 and the part 16. For example, in the embodiment as shown the biasing element 92 is a coil spring. The biasing element 92 may include a first end 112 and a second end 114, where the first end 112 of the biasing element 92 may be both mechanically and electrically connected to the hollow pin 90 and the second end 114 of the biasing element 92 may be both mechanically and electrically connected to the pin 94. The biasing element 92 exerts the biasing force upwardly in the direction D, which in turn urges the hollow pin 90 upwardly and towards the part 16. Thus, as seen in FIG. 6, the top surface 110 may abut against or otherwise establish electrical contact with the part 16. It is to be appreciated that the third electrical contact assembly 56 is spring-loaded or biased in order to accommodate for the various tolerance stack up between components.

FIG. 7 is an electrical schematic diagram of the WIF sensor 20 and the control module 86. As seen in FIG. 7, the two electrical contacts 50, 52 may be connected together by one or more resistors. Specifically, in the embodiment as shown, a resistor R1 is provided to connect the electrical contacts 50, 52. The resistor R1 may be used to attenuate any disturbance in a signal created between the electrical contacts 50, 52. As seen in FIG. 7, the resistor R1 may be a variable resistive element. The control module 86 may include an input circuit 120 and a signal return line having resistive elements R3 and R4. In the exemplary embodiment as shown in FIG. 7, the electrical contact 50 may be connected to the input circuit 120.

Referring generally to FIGS. 1-7, the disclosed WIF sensor provides an approach for dissipating the static electricity from the filter, without the need for other electrical components. Filter assemblies currently used typically have a grounding connector placed between the upper cap of the filter and another electrical component included within the housing such as a resistance heater, an electrical pump or a pressure sensor. However, linking the filter element to the ECU or another control module for grounding may not always be feasible if the canister does not include additional electrical features. Instead, the disclosed WIF sensor may be used to dissipate static electricity, and may be especially beneficial in situations where other electrical feature are not included within the housing.

Although the invention has been described and illustrated with respect to exemplary embodiments thereof, it should be understood by those skilled in the art that the foregoing and various other changes, omissions and additions may be made therein and thereto, without parting from the spirit and scope of the present invention. Accordingly, other embodiments are within the scope of the following claims.

What is claimed is:

1. A water in fuel (WIF) sensor, comprising:
a main body defining an upward facing surface:
a pair of electrical contacts each extending from the main body and terminating in a first end portion that is located above the upward facing surface of the main body, wherein a predetermined resistance flows between the electrical contacts when the first end portions of the pair of electrical contacts are submerged in water; and
a third electrical contact assembly having a first end portion extending from the main body and a second end portion extending to a connector cavity of the main body, wherein the first end portion of the third electrical contact assembly is located above the upward facing surface of the main body and extends beyond the first end portions of the pair of electrical contacts for engaging a grounding part, and wherein the second end portion of the third electrical contact assembly is connectable to a ground to discharge static electricity from the grounding part.

2. The WIF sensor of claim 1, wherein the third electrical contact assembly comprises a hollow pin, a biasing element, and a first pin, and wherein the hollow pin defines the first end portion of the third electrical contact assembly.

3. The WIF sensor of claim 2, wherein the biasing element is electrically connected to both the hollow pin and the first pin, and wherein the biasing element exerts a biasing force upon the hollow pin.

4. The WIF sensor of claim 2, wherein third electrical contact assembly comprises a second pin that is electrically connected to the first pin.

5. The WIF sensor of claim 2, wherein the second pin defines the second end portion of the third electrical contact assembly.

6. The WIF sensor of claim 2, wherein the second pin extends through the main body in a direction that is substantially perpendicular to the first pin.

7. The WIF sensor of claim 1, comprising at least one resistor for connecting the electrical contacts to one another.

8. The WIF sensor of claim 1, wherein the main body is constructed of a non-conductive material, and wherein a partition projects outward from the surface of the main body.

9. The WIF sensor of claim 8, wherein the wall provides a non-conductive barrier between the electrical contacts.

10. A fuel filtering system, comprising:
a filter including a grounding part;
a housing containing the filter, wherein the housing defines an aperture and wherein the grounding part is within the aperture; and
a water in fuel (WIF) sensor, wherein the aperture of the housing receives the WIF sensor, the WIF sensor comprising:
  a main body defining an upward facing surface, wherein the upward facing surface is located within the housing:
  a pair of electrical contacts each extending from the main body and terminating in a first end portion that is located above the upward facing surface of the main body, wherein a predetermined resistance flows between the electrical contacts when the first end portions of the pair of electrical contacts are submerged in water; and
  a third electrical contact assembly having a first end portion extending from the main body and a second end portion extending to a connector cavity of the main body, wherein the first end portion of the third electrical contact assembly is located above the upward facing surface of the main body and extends beyond the first end portions of the pair of electrical contacts and is electrically connected to the grounding part, and wherein the second end portion of the third electrical contact assembly is connectable to a ground to discharge static electricity from the grounding part.

11. The fuel filtering system of claim 10, comprising a control module electrically connected to the pair of electrical contacts and the third electrical contact assembly, and wherein the control module includes the ground.

12. The fuel filtering system of claim 11, wherein the filter includes a top end cap and a bottom end cap, wherein at least one of the bottom end cap and the bottom end cap is constructed of an electrically conductive material, and wherein the third electrical contact is electrically connected to an end cap of the filter element constructed of the electrically conductive material.

13. The fuel filtering system of claim 10, wherein the third electrical contact comprises a hollow pin, a biasing element, and a first pin, and wherein the hollow pin defines the first end portion.

14. The fuel filtering system of claim 13, wherein the biasing element is electrically connected to both the hollow pin and the first pin, and wherein the biasing element exerts a biasing force upon the hollow pin in a direction towards the filter element.

15. The fuel filtering system of claim 13, wherein third electrical contact assembly comprises a second pin that is electrically connected to the first pin.

16. The fuel filtering system of claim 13, wherein the second pin defines the second end portion of the third electrical contact assembly.

17. The fuel filtering system of claim 13, wherein the second pin extends through the main body in a direction that is substantially perpendicular to the first pin.

18. The fuel filtering system of claim 13, comprising at least one resistor for connecting the electrical contacts to one another.

19. The fuel filtering system of claim 10, wherein the main body is constructed of a non-conductive material, and wherein a partition projects outward from the surface of the main body.

20. The fuel filtering system of claim 10, wherein the wall provides a non-conductive barrier between the electrical contacts.

* * * * *